United States Patent
Amesbury et al.

(10) Patent No.: US 10,271,857 B2
(45) Date of Patent: Apr. 30, 2019

(54) SURGICAL INSTRUMENT

(71) Applicant: DEPUY IRELAND UNLIMITED COMPANY, Cork (IE)

(72) Inventors: Kevin Amesbury, Leeds (GB); Oliver Coultrup, Leeds (GB); David Thomas, Leeds (GB)

(73) Assignee: DEPUY IRELAND UNLIMITED COMPANY (R/F 040070/0868), Cork (IE)

(*) Notice: Subject to any disclaimer, the term of this patent is extended or adjusted under 35 U.S.C. 154(b) by 281 days.

(21) Appl. No.: 15/107,225

(22) PCT Filed: Dec. 17, 2014

(86) PCT No.: PCT/GB2014/053725
§ 371 (c)(1),
(2) Date: Jun. 22, 2016

(87) PCT Pub. No.: WO2015/097443
PCT Pub. Date: Jul. 2, 2015

(65) Prior Publication Data
US 2016/0331384 A1    Nov. 17, 2016

(30) Foreign Application Priority Data
Dec. 23, 2013  (GB) .................................. 1322923.2

(51) Int. Cl.
*A61B 17/15*    (2006.01)
(52) U.S. Cl.
CPC .................... *A61B 17/157* (2013.01)

(58) Field of Classification Search
CPC .................................................. A61B 17/157
See application file for complete search history.

(56) References Cited

U.S. PATENT DOCUMENTS

| 5,704,941 | A  | 1/1998  | Jacober |
| 6,645,215 | B1 | 11/2003 | McGovern |
| 8,226,658 | B2 | 7/2012  | Anthony |
| 8,758,354 | B2 | 6/2014  | Habegger |
| 9,232,951 | B2 | 1/2016  | Johannaber |

(Continued)

OTHER PUBLICATIONS

International Search Report for Corresponding International Application No. PCT/GB2014/053725 dated Mar. 5, 2015, 8 Pages.

(Continued)

*Primary Examiner* — Olivia C Chang (57) ABSTRACT

A spiked head assembly for a tibial jig for use during an orthopedic surgical procedure, includes a body and a mount for mounting the spiked head assembly on the tibial jig. The spiked head assembly comprises an elongate member having a central longitudinal axis, a first end and a second end and superior and inferior surfaces. The elongate member also has least one securing spike provided on the inferior surface towards the second end of the elongate member and configured to engage with a bone mass and arms extending from the elongate member in a direction perpendicular to the inferior surface. The arms are spaced apart from a plane that includes the central longitudinal axis and extends substantially perpendicularly to the inferior surface, so that the arms and the inferior surface define an access space for the surgical procedure.

9 Claims, 10 Drawing Sheets

(56) References Cited

U.S. PATENT DOCUMENTS

2012/0101504 A1* 4/2012 Habegger ............ A61B 17/151
 606/88
2014/0324054 A1 10/2014 Dmuschewsky

OTHER PUBLICATIONS

UK Search Report for Corresponding Application No. GB1322923.2, dated Aug. 14, 2014, 3 Pages.

* cited by examiner

SURGICAL INSTRUMENT

CROSS REFERENCE TO RELATED APPLICATION

This application is a National Stage 35 U.S.C. 371 of International Patent Application PCT/GB2014/053725 filed Dec. 17, 2014, claiming priority to United Kingdom applications GB1322923.2, filed Dec. 23, 2013 (now abandoned).

BACKGROUND OF THE INVENTION

The present invention relates to surgical instruments and in particular to a jig assembly used in orthopaedic surgery.

Knee replacement surgery is complex and requires the bone surfaces to be prepared. In particular femoral and tibial resectioning, in which a saw or other cutting tool is used to prepare bone surfaces to receive surgical implants, is required. In order to carry out these surgical techniques a number of tools and instruments can be used to assist the surgeon in carrying out the procedure appropriately.

A cutting block is usually used in order to guide the saw during the resection procedure. The cutting block is mounted and secured at the appropriate position on the bone surface. The correct positioning of the cutting block may be assisted by means of a jig and/or other alignment and support tools.

In the case of a tibial resectioning procedure, a tibial jig can be used in order to align a cutting block with respect to the longitudinal axis of the tibia. The tibial jig comprises a rod which can be in two parts to accommodate different tibia lengths. An appropriate cutting block is mounted on the rod, aligned at the proximal end of the tibia, and then secured in place by means of pins.

The cutting block defines an upper surface for guiding the cutting tool and may have a slot which can also be used as a cutting tool guiding surface. The slot can also be used as a means to attach other instruments such as a condylar stylus, or an alignment and adjustment tool. The jig may also include a mechanism for adjusting the flexion/extension slope of the cutting tool guiding surface.

One such tibial jig is the one designed for use with the Attune® knee prosthetic system from De Puy Synthes.

Some surgeons prefer to have the additional assistance provided by a spiked jig. The spiked jig that includes a rod which is aligned parallel to the tibia in the same way as the jig referred to above, but also includes a head which extends perpendicularly to the rod at a position that extends beyond the proximal end of the tibia at the knee joint. The head is mounted onto the rod by means of a mounting rod. The head includes a number of downwardly extending spikes which can be inserted into the tibia at the tibial eminence. One spike is longer than the other. During surgery, the surgeon is able to hammer only the longer spike in, make any adjustments to the rotation of the instruments that may be required, before hammering in the second, shorter spike. The cutting block is supported by the rod and mounted at an intermediate location on the tibia. The cutting block is therefore mounted partially along the rod rather than at the end as with the jig described above.

While the spiked jig provides additional stability for the surgeon, there are a number of disadvantages:

The positioning of the mounting rod obscures access to the cutting block, thus preventing the use of alignment rods which are secured to the cutting block.

It is not possible to provide a variable guiding surface slope mechanism because the presence of a mounting rod in front of the cutting block prevents this. It is therefore necessary to use additional blocks with guiding surfaces at predetermined and varying sloping angles which can be mounted onto the jig. This creates a large inventory of instrumentation If any further adjustments are required during the surgical procedure then this means that the whole spiked uprod needs to be removed to allow a cutting block change.

The profile of the head is such that a special condylar stylus is required in order to measure both tibial condyles.

BRIEF SUMMARY OF THE INVENTION

According to an aspect of the present invention, there is provided a spiked head assembly for attachment to a tibial jig for use during an orthopaedic surgical procedure, the assembly comprising a body and a mount, the body comprising:

an elongate member having a central longitudinal axis, a first end and a second end, superior and inferior surfaces, and at least one securing spike provided on the inferior surface towards the second end of the elongate member and configured to engage with a bone mass; and at least one arm extending from the elongate member in a direction perpendicular to the inferior surface; and wherein the mount is configured to attach the assembly to the tibial jig by the at least one arm, and the at least one arm is displaced from a plane that includes the central longitudinal axis and extends substantially perpendicularly to the inferior surface, such that the at least one arm and the inferior surface define an access space for the surgical procedure.

This assembly can be mounted onto a standard tibial jig at the end of the jig that is aligned with the cutting block. As the at least one arm is displaced or spaced apart from the plane which includes the central longitudinal axis of the elongate member which carries the at least one securing spike, an access space is defined between the at least one arm and the inferior surface of the elongate member thus allowing access to the slot in the cutting block. This means that the spiked head assembly does not need to be removed when access to the cutting block is required and additional tools such as a long leg alignment guide can be used.

The at least one arm and a side edge of the elongate member may be configured to subtend an acute angle.

This provides an assembly body which has a Z-shaped side profile. This enables the elongate member to have an increased length, and therefore increased strength and resistance to impact, while still enabling the at least one securing spike to be fixated in the tibial eminence. This is significant in view of the fact that the assembly will be required to be hammered in place when in use.

The body may comprise a first arm and a second arm, the first arm and the second arm both extending from the elongate member in the same direction substantially perpendicularly to the inferior surface, the first and second arms being displaced laterally from each other, and from the plane including the central longitudinal axis and extending substantially perpendicularly to the inferior surface, in opposing directions such that the access space is defined by the first arm, the second arm and the inferior surface.

The body may include a crosspiece connected between the first and second arms. The crosspiece may be U-shaped or T-shaped.

The mount may comprise a body having a pair of grooves provided on opposite sides of the body and arranged to receive respective terminating ends of the first and second arms.

The mount body may comprise a pair of hingedly connected body portions which, when in a closed position, are configured to clamp the mount to the tibial jig. The mount body may have an internal surface contour configured to match the contour of the outer surface of the tibial jig.

This provides a mount that enables the assembly to be detachably connected to the jig. Alternatively, the mount can be integral with the jig.

The elongate member may comprise a first part and a second part, the first part being attached to the at least one arm and the second part including the at least one securing spike and being detachably connected to the first part for slidable movement relative to the first part along the central longitudinal axis.

This enables the length of the elongate member to be adjusted to the required length.

The first part may include a grooved recess and the second part may include a lipped portion, the lipped portion being arranged to be receivable into the grooved recess for cooperation therewith, and the second part may include a securing means for securing the first part to the second part when the lipped portion is received into the grooved recess.

The securing means may be a rotatable knob that translates a bolt into and out of engagement with the floor of the grooved recess to secure the first part to the second part.

The knob may include a retaining pin to prevent the knob from being removed from the second part.

The elongate member may have a reduced profile at the second end.

By providing a reduced profile, it enables a standard condylar stylus to be mounted on the jig and pivoted to the appropriate location on the condyle. As the stylus tip can be moved over the elongate body both condyles can be checked in a single operation.

According to another aspect of the invention, there is provided a tibial jig for use in an orthopaedic surgical procedure, the tibial jig including a rod having a longitudinal axis, a cutting block detachably connected to the rod, and a spiked head assembly connected to the rod towards an end of the rod, the spiked head assembly comprising a body and a mount, the body having:
  an elongate member having a central longitudinal axis, a first end and a second end, superior and inferior surfaces, and at least one securing spike provided on the inferior surface towards the second end of the elongate member and configured to engage with a bone mass; and
  at least one arm extending from the elongate member in a direction substantially perpendicularly to the inferior surface; and
  wherein the mount is configured to attach the spiked head assembly to the tibial jig by the at least one arm, and the at least one arm is displaced laterally of the longitudinal axis of the rod, such that the at least one arm and the inferior surface define an access space for the surgical procedure.

The body may comprise a first arm and a second arm, the first arm and the second aim both extending from the elongate member in the same direction substantially perpendicularly to the inferior surface, the first and second arms being displaced laterally from each other and from the longitudinal axis of the rod such that the access space is defined by the first arm, the second arm and the inferior surface.

According to third aspect, there is provided a spiked head assembly for attachment to a tibial jig for use during an orthopaedic surgical procedure, the assembly comprising a body and a mount, the body comprising:
  an elongate member having a central longitudinal axis, a first end and a second end, superior and inferior surfaces, and at least one securing spike provided on the inferior surface towards the second end of the elongate member and configured to engage with a bone mass; and
  at least one arm extending from the elongate member in a direction perpendicular to the inferior surface; and
  wherein the mount is configured to attach the assembly to the tibial jig by the at least one arm, and the at least one arm and a side edge of the elongate member may be configured to subtend an acute angle.

According to another aspect of the invention, there is provided a spiked head assembly for attachment to a tibial jig for use during an orthopaedic surgical procedure, the assembly comprising a body which comprises an elongate member having a central longitudinal axis, a first end and a second end, superior and inferior surfaces, and at least one securing spike provided on the inferior surface towards the second end of the elongate member and configured to engage with a bone mass; and at least one arm extending from the elongate member in a direction perpendicular to the inferior surface, and in which the at least one arm is spaced apart from a plane that includes the central longitudinal axis and extends substantially perpendicularly to the inferior surface, such that the at least one arm and the inferior surface define an access space for the surgical procedure.

BRIEF DESCRIPTION OF THE DRAWINGS

The invention will now be described, by way of example only, with reference to the following figures, of which.

DETAILED DESCRIPTION OF THE INVENTION

A spiked head assembly 100 for a tibial jig 101 comprises a main body 1 and a mount 25.

The main body 1 comprises an elongate member 2 having a central longitudinal axis X, a first end 3, and a second end 4, a superior surface 5 and an inferior surface 6. The elongate member 2 has side edges 28a, 28b.

The main body 1 has a pair of arms, comprising a first arm 10a and a second arm 10b, attached to, and extending from, the first end 3 of the elongate member 2. The first arm 10a, and the second arm 10b extend from the first end 3 at a respective side edge 28a, 28b of the elongate member 2, such that the first arm 10a, and the second arm 10b are spaced apart from each other.

The first end 3 of the elongate member 2, being proximal to the point of attachment between the elongate member 2 and the pair of arms 10a, 10b, is a proximal end, and the second end 4 is a distal end of the elongate member 2, being the end away from this point of attachment between the elongate member and the pair of arms 10a, 10b.

Figure 2:
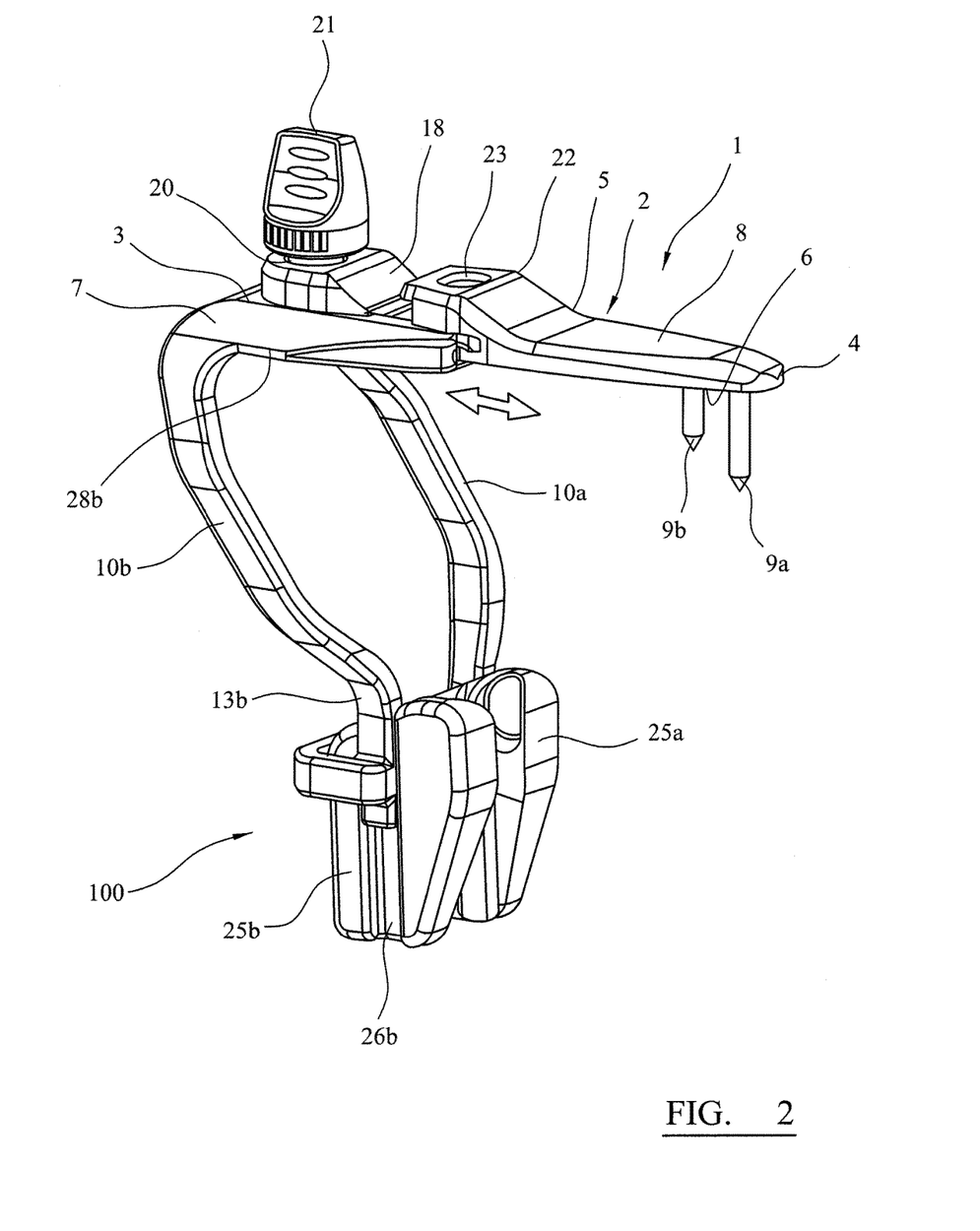
FIG. 2 is second perspective view of the spiked head assembly for a tibial jig.

The elongate member 2 comprises a first part 7 and a second part 8, the second part 8 being slidable with respect to the first part 7 as indicated by the double-headed arrow in FIG. 2.

The first part 7 includes the first end 3 of the elongate member 2 and the second part 8 includes the second end 4 of the elongate member 2. Extending substantially perpendicularly from the inferior surface 6 towards the second end 4 are a pair of spiked pins 9a, 9b. One of the pins 9a is longer than the other 9b.

As a consequence of the cooperation of the first part 7 and the second part 8, the inferior surface 6 has a stepped profile at the point where the first part 7 ends.

Figure 1:
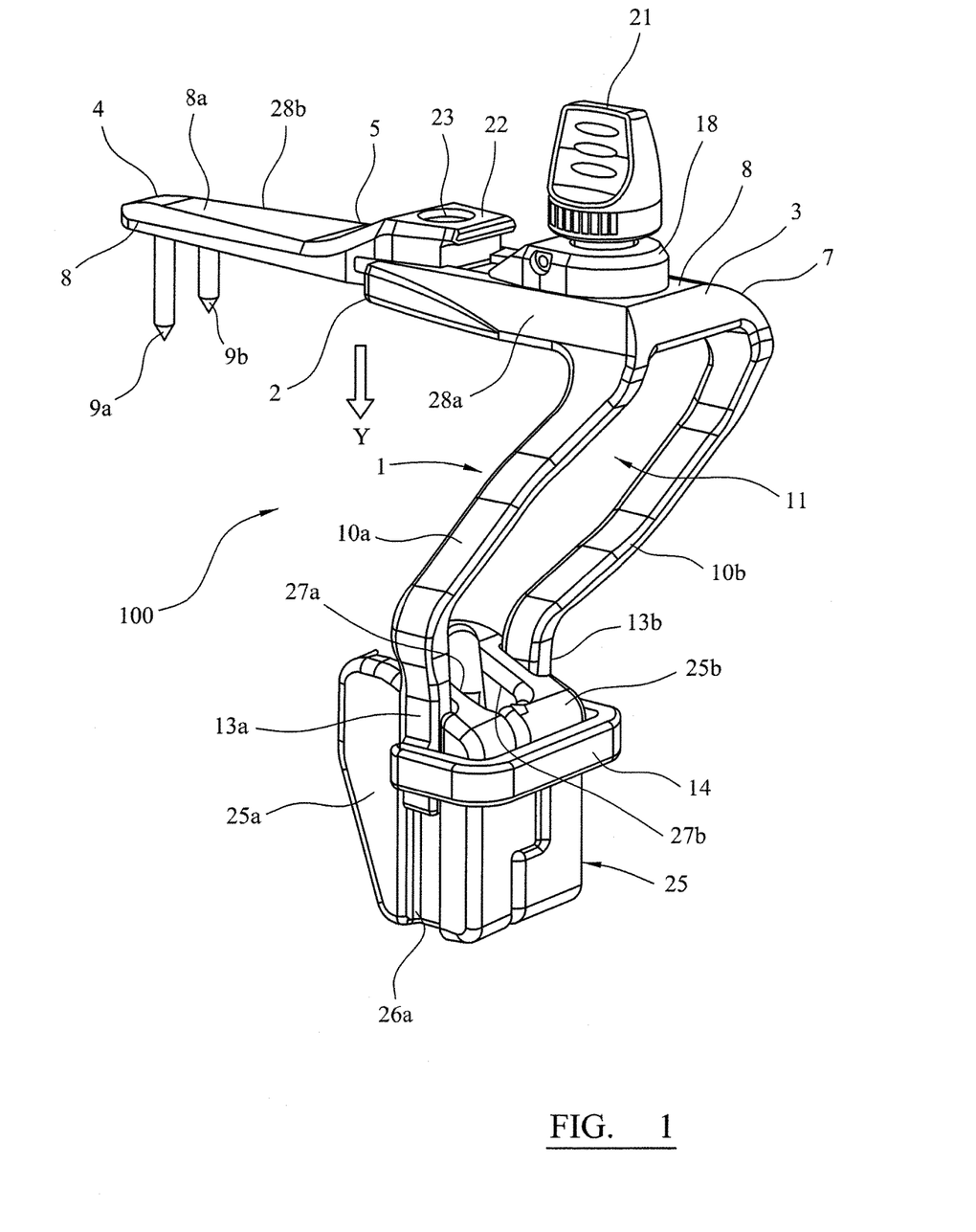
FIG. 1 is a first perspective view of the spiked head assembly for a tibial jig.
Figure 5:
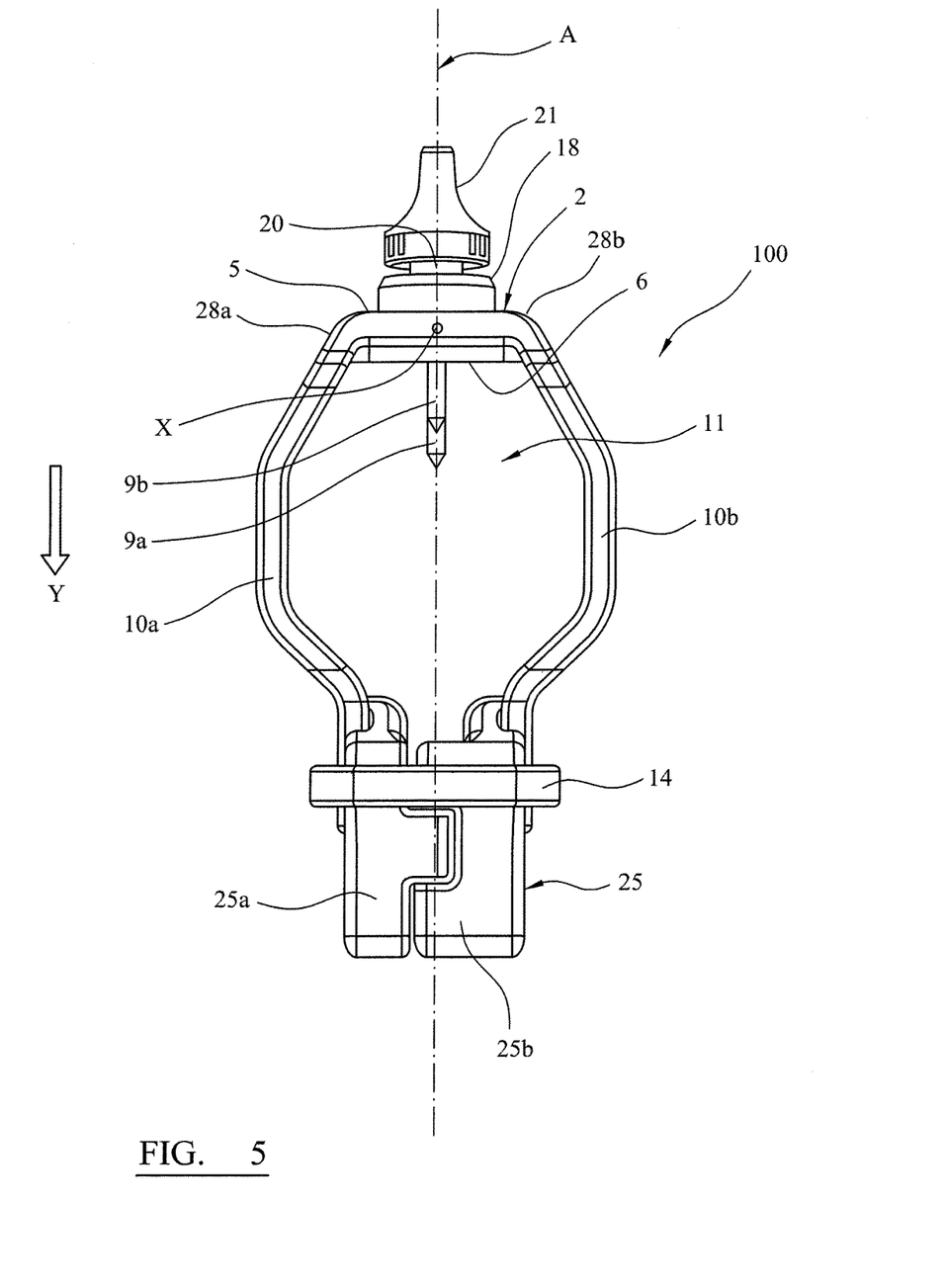
FIG. 5 is a rear view of the assembly of FIGS. 1 and 2.
Figure 6:
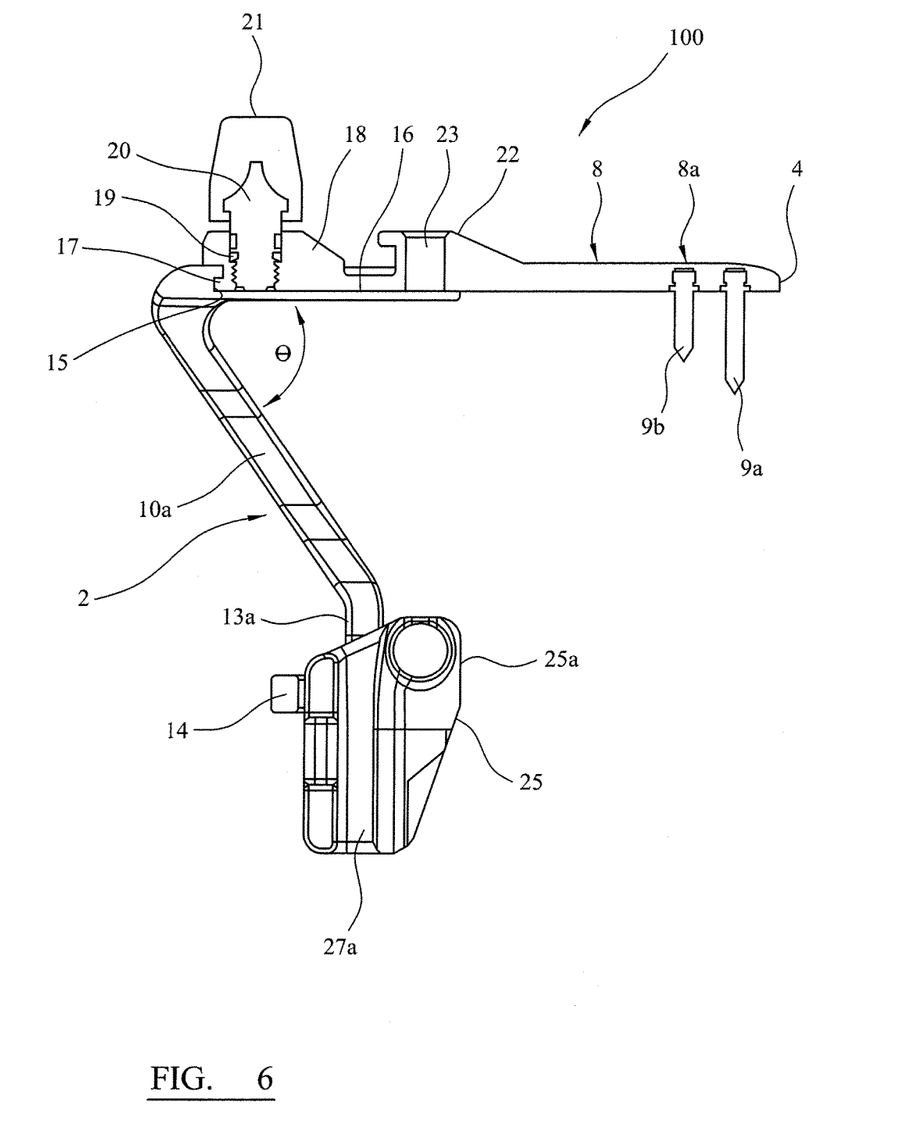
FIG. 6 is a side view of the assembly.
Figure 7:
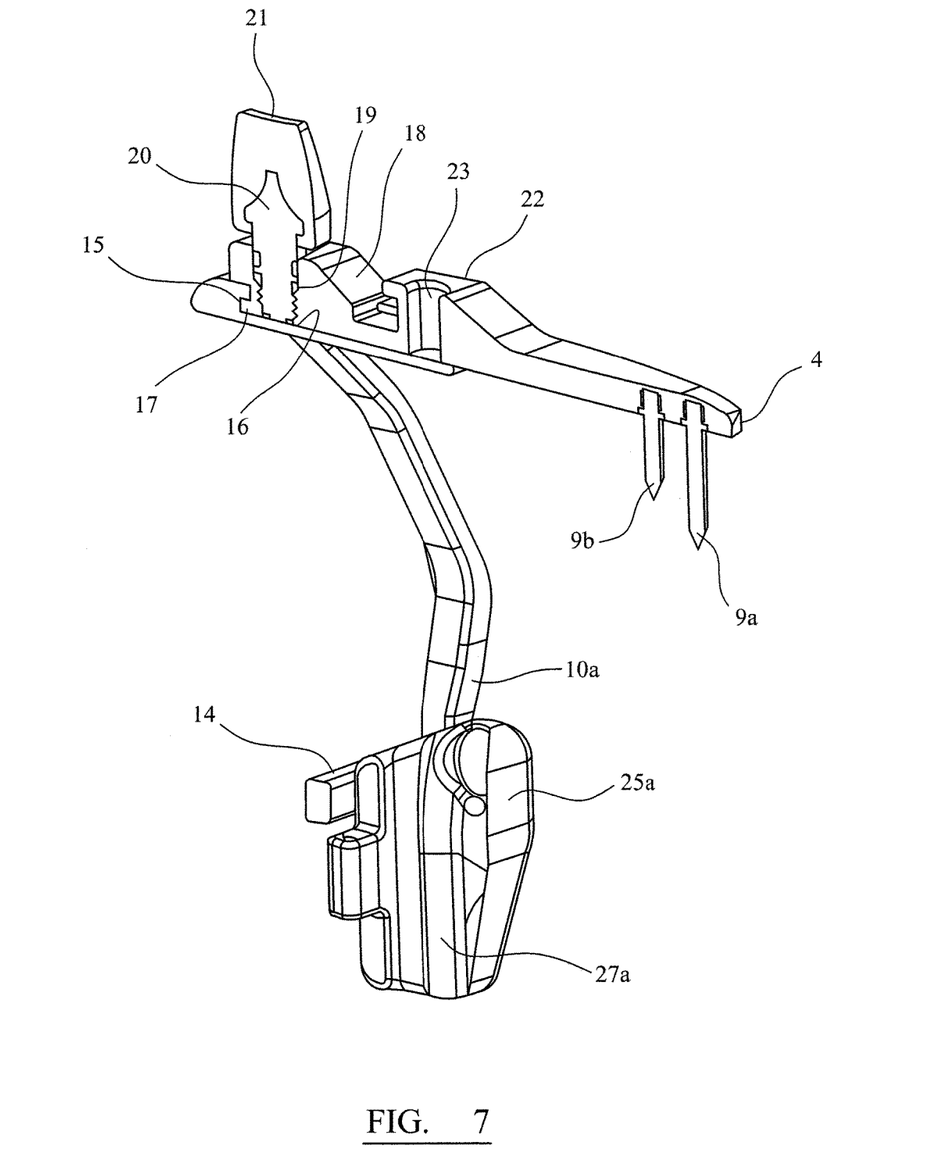
FIG. 7 is a perspective cross section through the assembly of FIGS. 1 and 2.
Figure 8:
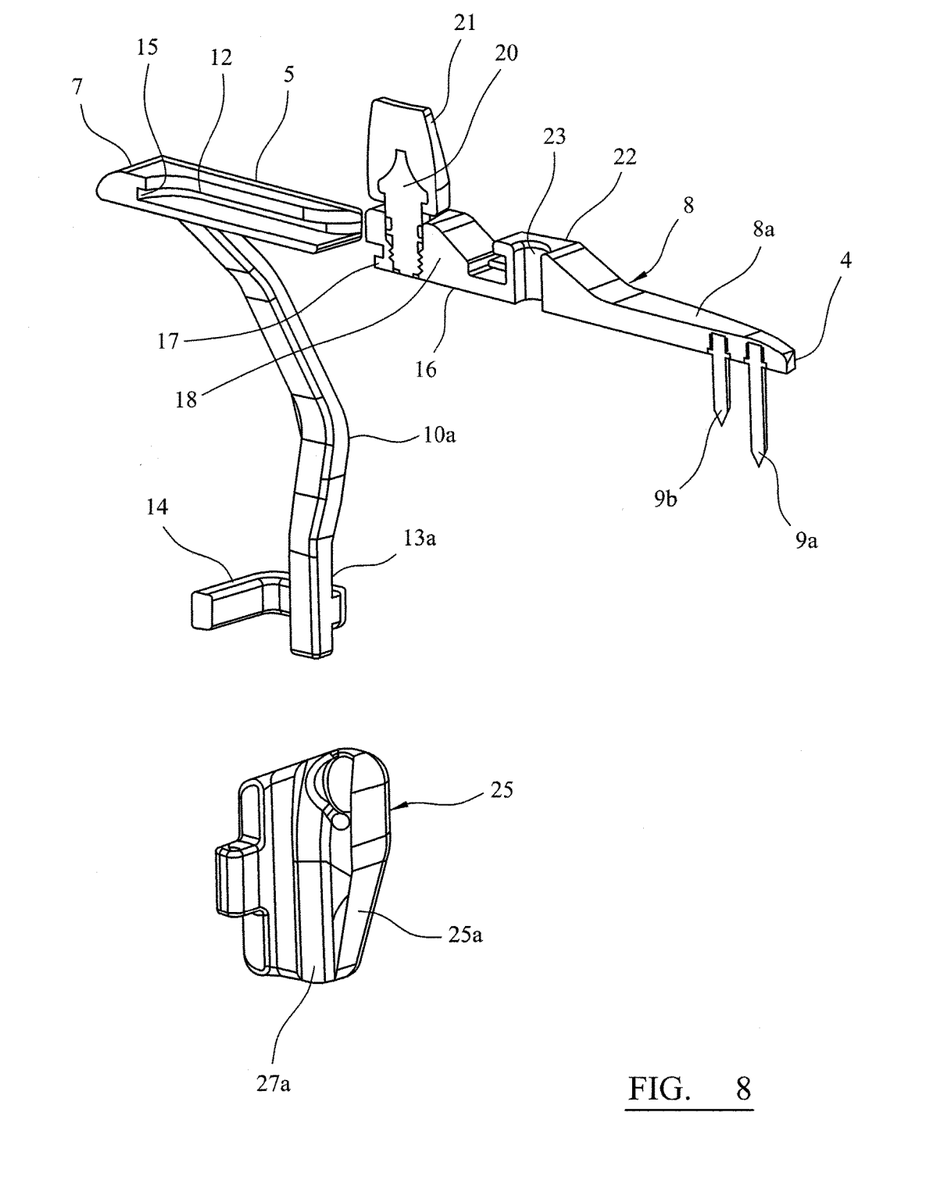
FIG. 8 is an exploded cross-section of corresponding to FIG. 7.
Figure 9:
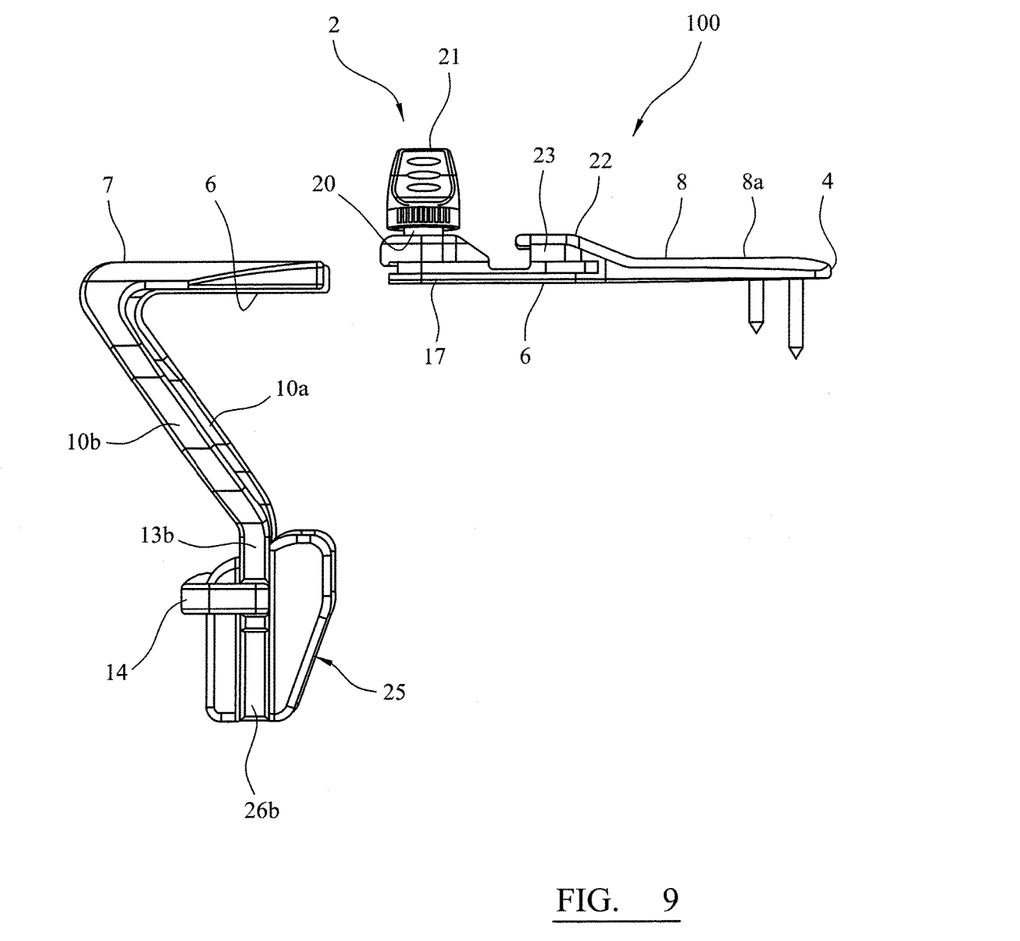
FIG. 9 is an exploded side view of the assembly.
Figure 10:
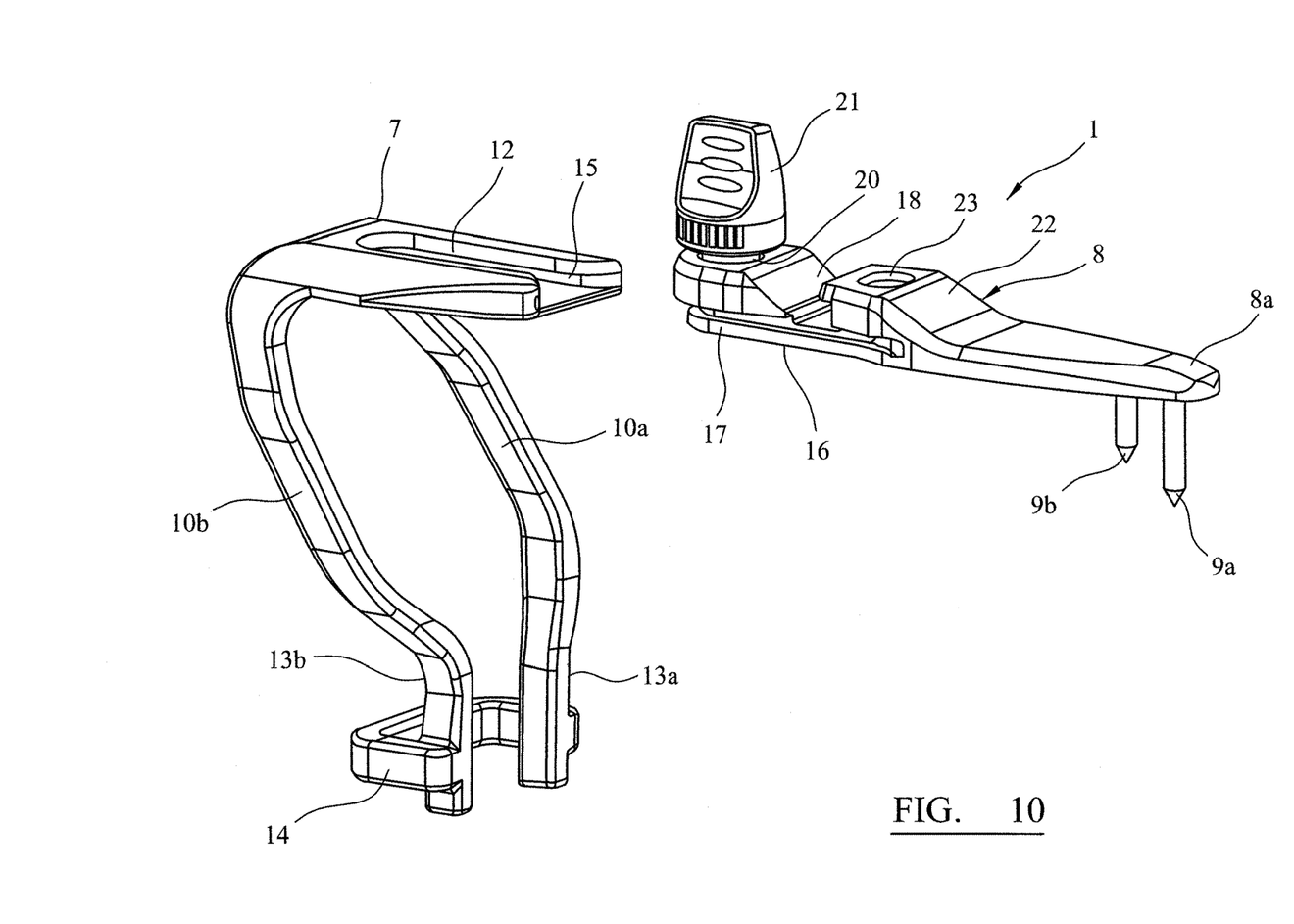
FIG. 10 is an exploded perspective view of the main body of the assembly of FIG. 1.

Each of the first and second arms 10a, 10b subtend an acute angle θ to the respective side edges 28a, 28b of the elongate member 2, but extend in a direction substantially perpendicularly to the inferior surface 6 as indicated by the arrow Y in FIGS. 1 and 5. Each of the first and second arms 10a, 10b therefore present a Z-shaped profile as viewed from the side—see, for example, FIG. 6.

The first and second arms 10a, 10b follow a curved or bowed profile as viewed from the ends of the assembly 1, as can be seen in FIG. 5.

Each of the first and second arms 10a, 10b terminates in a straight end segment 13a, 13b.

A U-shaped crosspiece 14 extends perpendicular to, and between, the end segments 13a, 13b.

Relative to a plane A, which includes the central longitudinal axis X and intersects the superior and inferior surfaces 5, 6, and which is substantially perpendicular to the inferior surface 6, the first and second arms 10a, 10b are spaced apart, laterally of each other, and of this transverse plane A—one arm 10a, 10b on either side of the plane A. This is illustrated in FIG. 5.

The first and second arms 10a, 10b and the inferior surface 6 define an access space 11 for the assembly 1.

The access space 11 therefore comprises the space bounded by the inferior surface 6, extending from the first end 3 of the elongate member 2, and the first and second arms 10a, 10b. The access space 11 is accessible through the space defined by the spaced apart first and second arms 10a, 10b.

The first part 7 of the elongate member 2 includes a longitudinal U-shaped recess 12 in the superior surface 5. The U-shaped recess 12 has an internal groove 15 around the perimeter of the U-shaped recess 12.

The second part 8 of the elongate member 2 includes a tongue portion 8a which includes the second end 4 and a U-shaped rear portion 16 which has a lip 17 extending around the perimeter of the U-shaped rear portion 16. The U-shaped rear portion 16 is dimensioned so as to cooperate with the U-shaped recess 12 in the first part 7 so that the lip 17 can be received into the groove 15 in the U-shaped recess 12.

In this way, the first part 7 and the second part 8 can be connected together and the second part 8 is able to slide relative to the first part 7 along the central longitudinal axis X of the elongate member 2.

The tongue portion 8a has a reduced height profile at the second end 4.

The U-shaped rear portion 16 has a raised region 18 with a threaded cylindrical aperture 19 into which a threaded bolt 20 can be received. A knob 21 attached to the threaded bolt 20 can be used to manually turn the threaded bolt 20 when engaged in the threaded cylindrical aperture 19 to translate the bolt 20 within the cylindrical aperture 19 so that the bolt 21 can engage the floor of the U-shaped recess 12 so as to lock the second part 8 in position relative to the first part 7 of the elongate member 2. By turning the bolt 21 in the opposite direction the bolt will disengage from the floor of the U-shaped recess 12 to allow the second part to be slidable moved relative to the first part 7 of the elongate member 2 again. A retaining pin (not shown) is provided to prevent the knob 21 from being removed from the second part 8.

The second part 8 also includes a raised section 22 with a second circular aperture 23 provided therein. When the second part 8 is fully received into the U-shaped recess 12, the second circular aperture 23 can be used to receive an impaction/extraction tool (not shown) as will be described in further detail below.

The mount 25 mounts the assembly 100 to the tibial jig 101.

Figure 3:
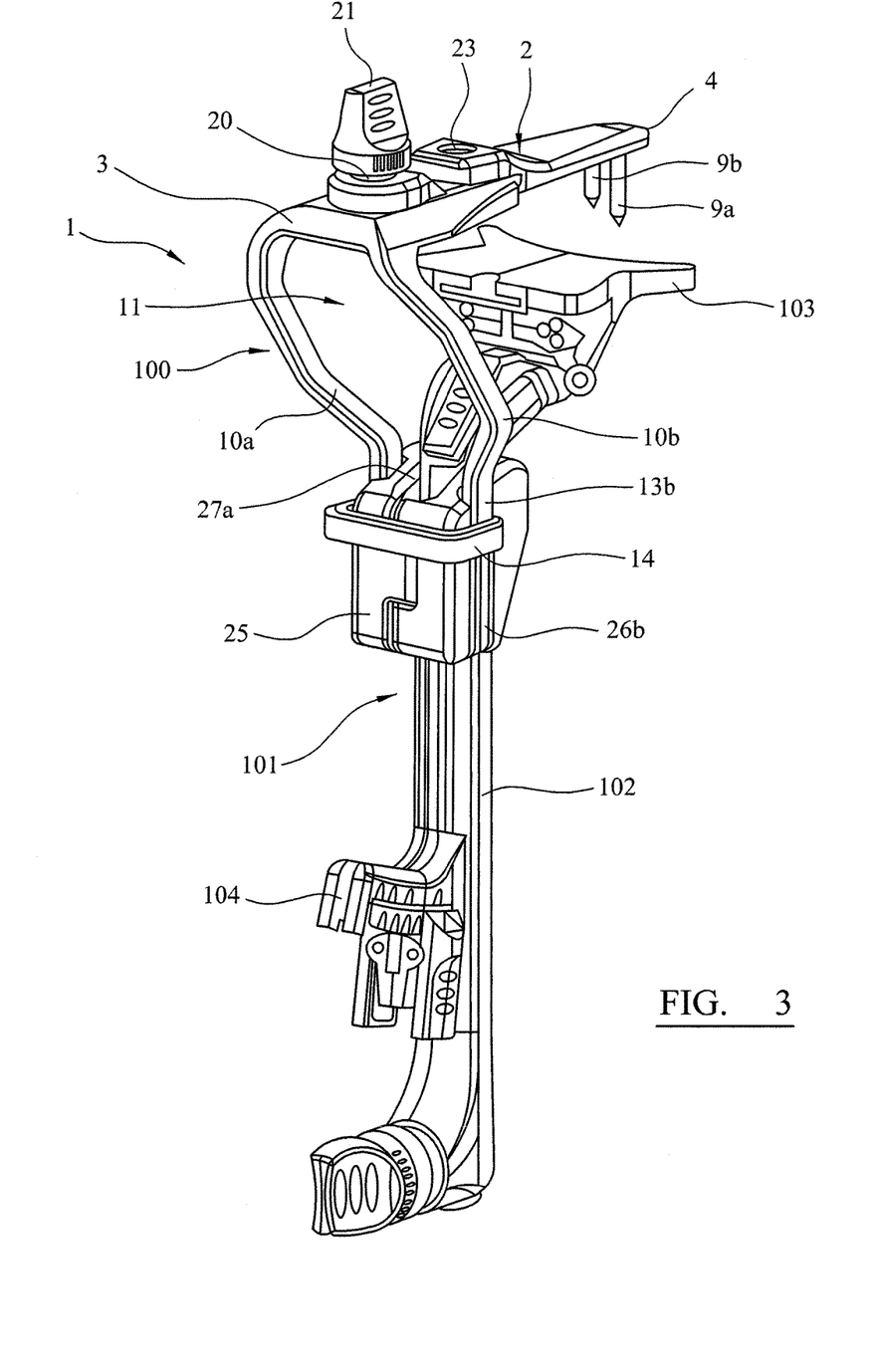
FIG. 3 is a perspective view of a tibial jig with the spiked head assembly of FIGS. 1 and 2 attached.
Figure 4:
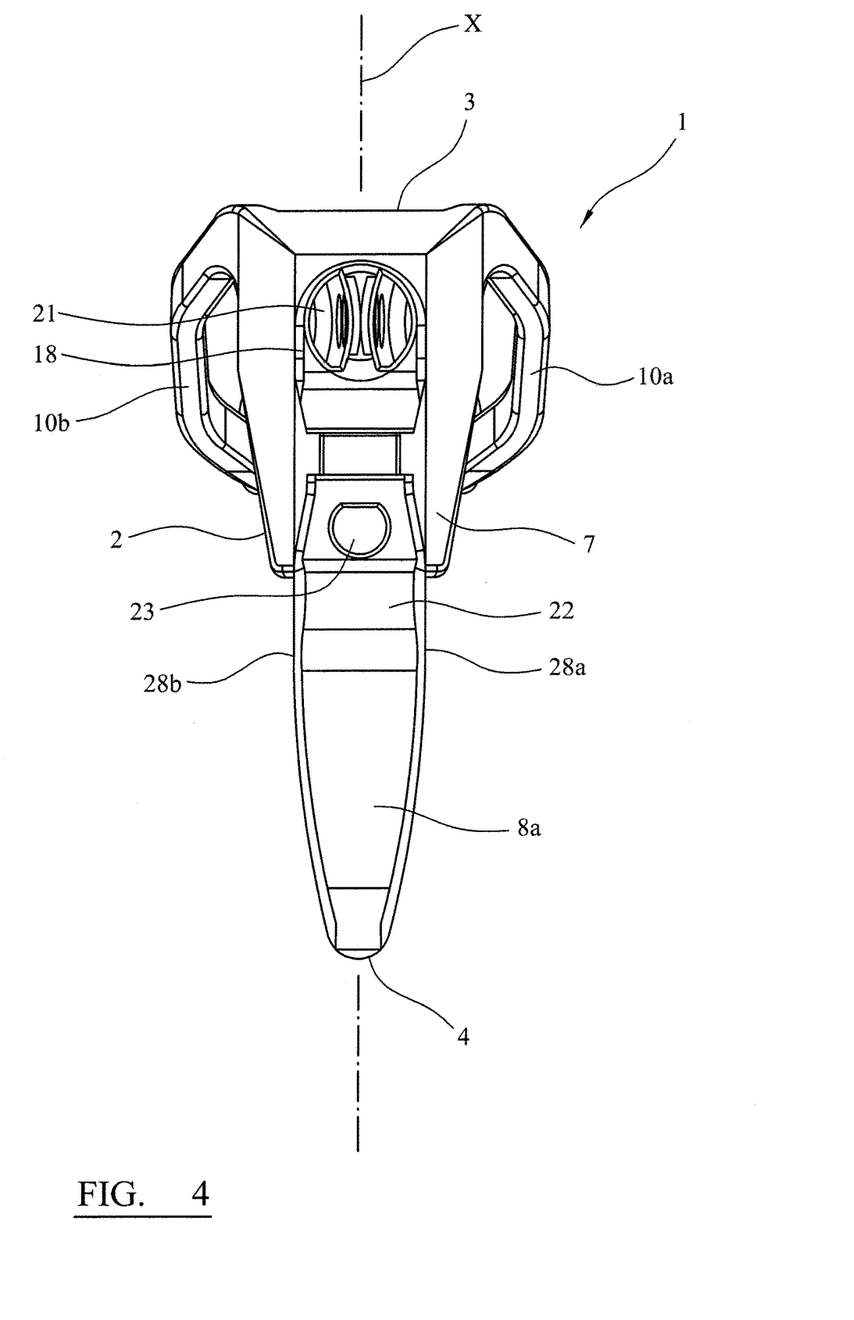
FIG. 4 is a plan view of the assembly of FIG. 1.

The tibial jig is illustrated in FIG. 3 and comprises an elongate tibial jig body 102 and a cutting block 103.

The mount 25 comprises a body formed from two hingedly connected body portions 25a, 25b. Each of the body portions 25a, 25b has a groove 26a, 26b running lengthways along one side of the respective body portion 25a, 25b and a curved recesses 27a, 27b on the opposite side of the respective body portion 25a, 25b.

When the body portions 25a, 25b are oriented in a closed position, the curved recesses 27a, 27b define a matching internal surface contour in which the elongate tibial jig body 102 can be received. In this way, when in the closed position, the body portions 25a, 25b clamp around the elongate jig body 102 so as to secure the mount 25 to the tibial jig body 102. This is illustrated in FIG. 3. The matching surface contour can be selected depending upon the profile of the tibial jig body 102 as long as it enables the mount 25 to be clamped around the tibial jig body 102.

When in the closed position, the grooves 26a, 26b are aligned substantially parallel with each other on opposite sides of the mount 25 as shown, for example, in FIGS. 1, 2 and 3.

To assemble the main body 1 on the mount 25, the body portions 25a, 25b are in the closed position and the straight end segments 13a, 13b of the arms 10a, 10b are received into respective grooves 26a, 26b as illustrated in FIGS. 2 and 3.

The U-shaped crosspiece 14 encloses the mount 25 at the hinged connection between the body portions 25a, 25b thus serving to keep the mount 25 in the closed position. In an alternative, the crosspiece can be T-shaped.

In use, the mount 25 is attached to the tibial jig body 102 as described above. The position of the mount 25 along the length of the tibial jig body 102 can be selected dependent upon the required bone section. The tibial jig body 102 is secured to a patient's lower leg (not shown) in the usual way. The main body 1 is then attached to the mount 25 by inserting the straight end segments 13a. 13b into the respective grooves 26a, 26b. In this way, the arms 10a, 10b are spaced apart, laterally of the longitudinal axis of the tibial jig body 102.

The elongate member 2 can then be adjusted by sliding the first part 7 relative to the second part 8 so as to adjust the position of the spiked pins 9a, 9b as required. When in position the spiked pins 9a, 9b are hammered into position in accordance with known surgical techniques.

If the tibial jig 101 is provided with a cutting tool slope adjustment mechanism 104, as shown in FIG. 3, then this can be manipulated to select the correct slope for the cutting tool.

As described above, the access space 11 is defined by the inferior surface 6 of the elongate body 2 and the first and second arms 10a, 10b, with access to the access space 11 being available through the separation between the spaced apart first and second arms 10a, 10b.

The access space 11 is then available for a surgeon to access the cutting block 103 for use with any required tools to carry out the necessary alignments as is well known in the art. If required, a condyle stylus can be mounted on the cutting block 103. Because of the reduced profile of the second end 4 of the elongate member 2, the condyle stylus can pivoted between condyles without being obstructed by the elongate member 2.

Once the alignment of the tibial jig 101 is selected, then the assembly 100 can be removed by removing the body 2 from the mount 25 and then unclamping the mount 25 from the tibial jig body 102.

The tibia can then be resected in accordance with known surgical techniques.

The assembly 100 can be made of medical grade stainless and/or medical grade polymers as required. Other suitable materials may also be used.

In an alternative, only a single arm 10a, 10b could be provided on the elongate member 2 with the access space 11 being defined by the arm 10a, 10b and the inferior surface 6.

The invention claimed is:

1. A spiked head assembly for attachment to a tibial jig for use during an orthopaedic surgical procedure, the spiked head assembly comprising:
   (a) a body which comprises an elongate member having a central longitudinal axis, a first end and a second end, superior and inferior surfaces, and at least one securing spike provided on the inferior surface towards the second end of the elongate member and configured to engage with a bone mass; and at least one arm extending from the elongate member in a direction perpendicular to the inferior surface; and
   (b) a mount on the at least one arm which is configured to attach the assembly to the tibial jig,
   in which:
   the arm has an end and an inner surface;
   the mount is secured to the end of the arm at a position spaced from the inferior surface of the elongate member;
   the at least one arm is spaced apart from a plane that includes the central longitudinal axis and extends substantially perpendicularly to the inferior surface, such that the at least one arm, the mount and the inferior surface define an access space for the surgical procedure; and
   the access space extends across the plane from the inferior surface to the mount and from the inner surface of the arm and continues across the plane.

2. The spiked head assembly according to claim 1, wherein the at least one arm and a side edge of the elongate member are configured to subtend an acute angle.

3. The spiked head assembly according to claim 1, wherein the body comprises a first arm and a second arm, the first arm and the second arm both extending from the elongate member in the same direction substantially perpendicularly to the inferior surface, the first and second arms being spaced apart laterally from each other, and from the plane including the central longitudinal axis and which extends substantially perpendicularly to the inferior surface, such that the access space is defined by the first arm, the second arm, the mount and the inferior surface.

4. The spiked head assembly according to claim 3, wherein the body includes a crosspiece connected between the first and second arms.

5. The spiked head assembly according to claim 3, wherein the mount comprises a body having a pair of grooves provided on opposite sides of the body and arranged to receive respective terminating ends of the first and second arms.

6. The spiked head assembly according to claim 5, wherein the mount body comprises a pair of body portions which, when in a closed position are configured to clamp the mount to the tibial jig.

7. The spiked head assembly according to claim 1, wherein the elongate member comprises a first part and a second part, the first part being attached to the at least one arm and the second part including the at least one securing spike and being detachably connected to the first part for slidable movement relative to the first part along the central longitudinal axis.

8. The spiked head assembly according to claim 7, wherein the first part includes a grooved recess and the second part includes a lipped portion, the lipped portion being arranged to be receivable into the grooved recess for cooperation therewith, the second part including a securing means for securing the first part to the second part when the lipped portion is received into the grooved recess.

9. The spiked head assembly according to 1, wherein the elongate member has a reduced profile at the second end.

* * * * *